United States Patent
Gensler et al.

(10) Patent No.: US 7,327,068 B2
(45) Date of Patent: Feb. 5, 2008

(54) SENSORS AND RELATED DEVICES AND METHODS

(75) Inventors: Jeffrey Alan Gensler, Austin, TX (US); Mark Moses Koeroghlian, Austin, TX (US); Keith Andrew Kunz, Austin, TX (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 332 days.

(21) Appl. No.: 11/049,016

(22) Filed: Feb. 2, 2005

(65) Prior Publication Data

US 2006/0170312 A1 Aug. 3, 2006

(51) Int. Cl.
| | |
|---|---|
| *H01L 41/053* | (2006.01) |
| *H03H 9/10* | (2006.01) |
| *G01N 33/566* | (2006.01) |
| *C12Q 1/68* | (2006.01) |

(52) U.S. Cl. .................. 310/313 R; 310/338; 310/348
(58) Field of Classification Search ........ 310/311–371, 310/800
See application file for complete search history.

(56) References Cited

U.S. PATENT DOCUMENTS

| | | | | |
|---|---|---|---|---|
| 4,216,401 A | * | 8/1980 | Wagner .................. 310/313 R |
| 4,317,372 A | * | 3/1982 | Hartemann .................. 73/703 |
| 4,399,686 A | | 8/1983 | Kindlund et al. .......... 73/24.06 |
| 4,789,804 A | * | 12/1988 | Karube et al. .............. 310/311 |
| 4,895,017 A | | 1/1990 | Pyke et al. ................. 73/24.06 |
| 4,932,255 A | * | 6/1990 | Brace et al. ............. 73/204.11 |
| 5,012,668 A | | 5/1991 | Haworth .................... 73/24.06 |
| 5,216,312 A | * | 6/1993 | Baer et al. .............. 310/313 D |
| 5,239,715 A | | 8/1993 | Wagner ......................... 5/717 |
| 5,289,715 A | | 3/1994 | Staples et al. ............. 73/24.01 |
| 5,325,704 A | | 7/1994 | Mariani et al. ........... 73/24.06 |
| 5,571,944 A | | 11/1996 | Pfeifer et al. ............. 73/24.04 |
| 5,817,922 A | | 10/1998 | Rapp et al. ................ 73/24.06 |

(Continued)

FOREIGN PATENT DOCUMENTS

EP 0 509 328 10/1992

(Continued)

OTHER PUBLICATIONS

"Chemical sniffer relies on SAW-based technology," *Electronic Engineering Times*, Jul. 24, 2000.

(Continued)

*Primary Examiner*—Thomas M. Dougherty
(74) *Attorney, Agent, or Firm*—Fulbright & Jaworski LLP; Mark Garrett

(57) ABSTRACT

Sensors that include SAW devices, related methods, and related devices. Many embodiments are included. Some of the present sensors include an inlet structure; a mounting structure that is spaced apart from the inlet structure, the mounting structure having a top surface and an opposing bottom surface; and surface acoustic wave (SAW) devices disposed on the top surface of the mounting structure; where (a) the mounting structure includes openings that extend from the top surface to the bottom surface through which fluid can flow that has first passed over the SAW devices during operation of the sensor, or (b) the mounting structure and SAW devices together define openings through which fluid can flow that has first passed over the SAW devices during operation of the sensor.

17 Claims, 11 Drawing Sheets

U.S. PATENT DOCUMENTS

| | | | |
|---|---|---|---|
| 5,918,258 A * | 6/1999 | Bowers | 73/24.06 |
| 6,029,500 A * | 2/2000 | Tom | 73/31.05 |
| 6,122,954 A | 9/2000 | Bowers | 73/24.06 |
| 6,134,944 A | 10/2000 | Yu et al. | 73/23.35 |
| 6,269,703 B1 | 8/2001 | Bowers | 73/863.12 |
| 6,321,588 B1 | 11/2001 | Bowers et al. | 73/24.01 |
| 6,354,160 B1 * | 3/2002 | Staples et al. | 73/863.12 |
| 6,656,738 B1 | 12/2003 | Vogel et al. | 436/161 |
| 6,701,774 B2 | 3/2004 | Srinivasan et al. | 73/23.42 |
| 6,962,675 B2 * | 11/2005 | Lewis et al. | 422/83 |
| 2002/0017125 A1 * | 2/2002 | Lewis et al. | 73/31.05 |
| 2003/0000291 A1 | 1/2003 | Kolosov et al. | 73/61.52 |
| 2004/0072208 A1 * | 4/2004 | Warthoe et al. | 435/6 |
| 2006/0024813 A1 * | 2/2006 | Warthoe | 435/287.1 |

FOREIGN PATENT DOCUMENTS

| | | |
|---|---|---|
| WO | WO 01/16091 | 3/2000 |
| WO | WO 01/36934 | 5/2001 |

OTHER PUBLICATIONS

"Sandia's tiny acoustic wave sensors will detect minute traces of dangerous chemicals," Sandia National Laboratories, www.sciencedaily.com/releases/199/03/990331063123.htm, 1999.

Brown, "Single-chip hydrocarbon sensor explored," *Electronic Engineering Times*, Jan. 15, 1996.

Clarke, "For electronic nose, 2 heads better than 1," *Electronic Engineering Times*, pp. 37, Dec. 5, 1994.

Drafts, "Acoustic wave technology sensors," *Sensors*, 2000.

Johnson, "Biodetector looks to MEMS for desktop shrink," *Electronic Engineering Times*, pp. 5, Mar. 18, 2002.

Johnson, "World's first handheld chemical system slated for fourth quarter- Sandia puts GaAs sensors onto 'lab-on-a-chip'," *Analytical Chemistry*, 36:1735-1739, 1964.

King, "Piezoelectric sorption dector," *Analytical Chemistry*, 36:1735-1739, 1964.

Rapp et al., "Development of an analytical microsystem for organic gas detection based on surface acoustic wave resonators," *Fresenius' Journal of Analytical Chemistry*, 352:699-704, 1995.

Staples, "Nerve gas detection," EST Internal Technical Paper, pp. 1-11, 1998.

Wu, "A piezoelectric biosensor as an olfactory receptor for odour detection: electronic nose," *Biosensors and Bioelectronics*, 14:9-18, 1999.

\* cited by examiner

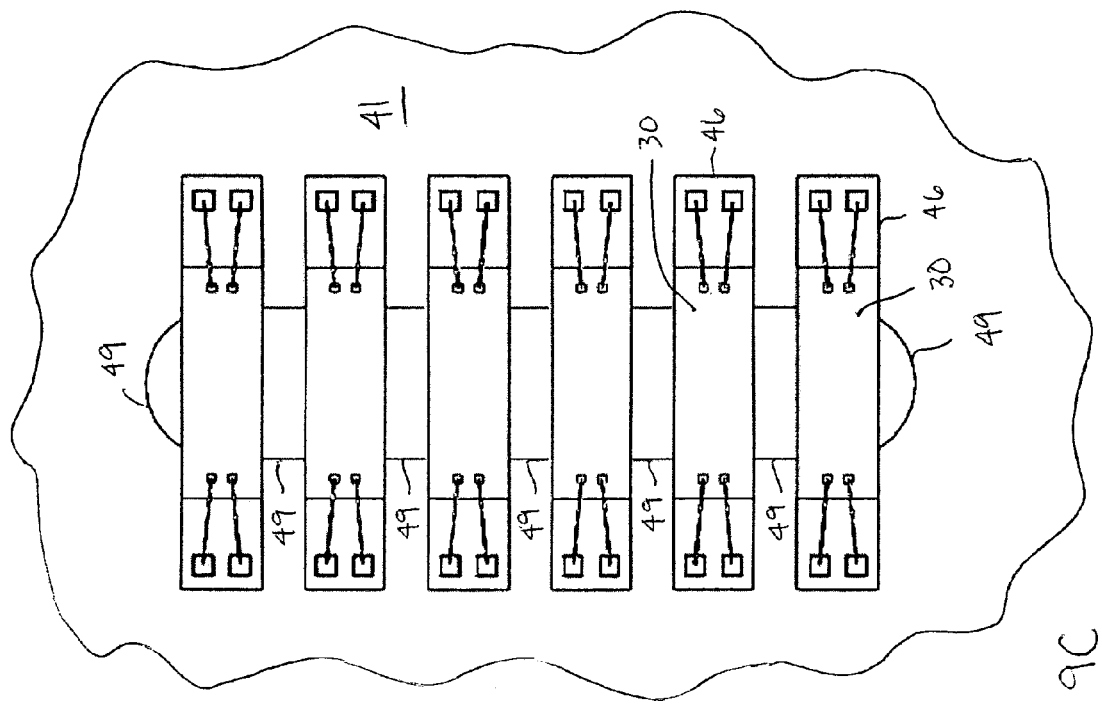
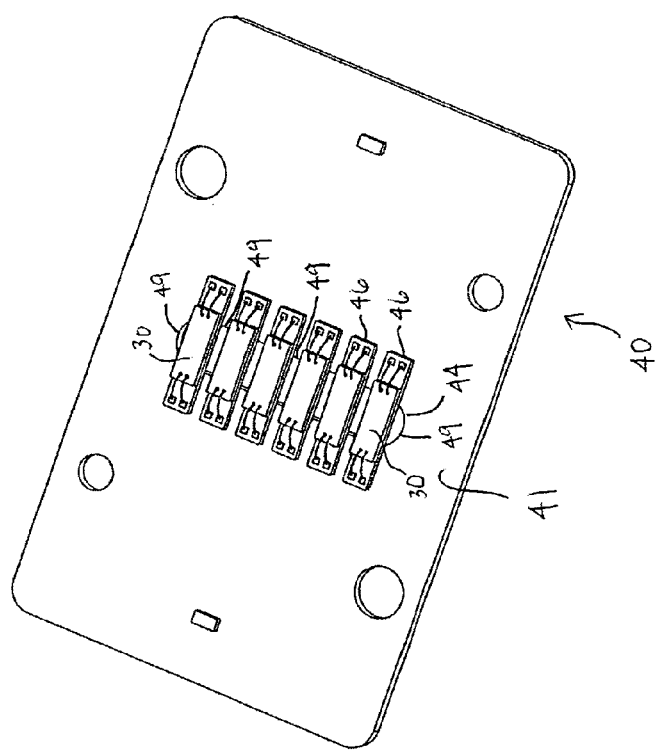
FIG. 9B
FIG. 9C

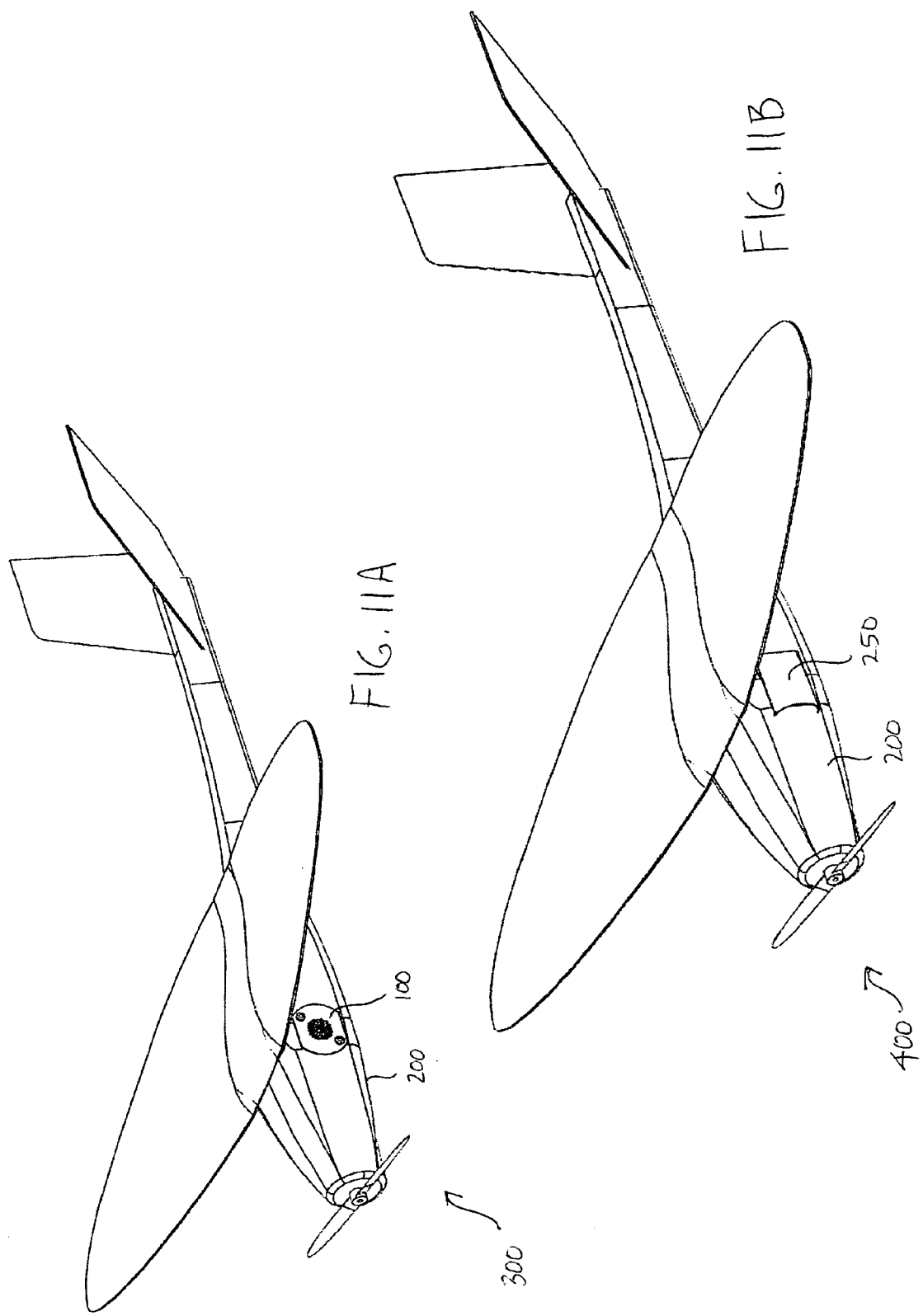

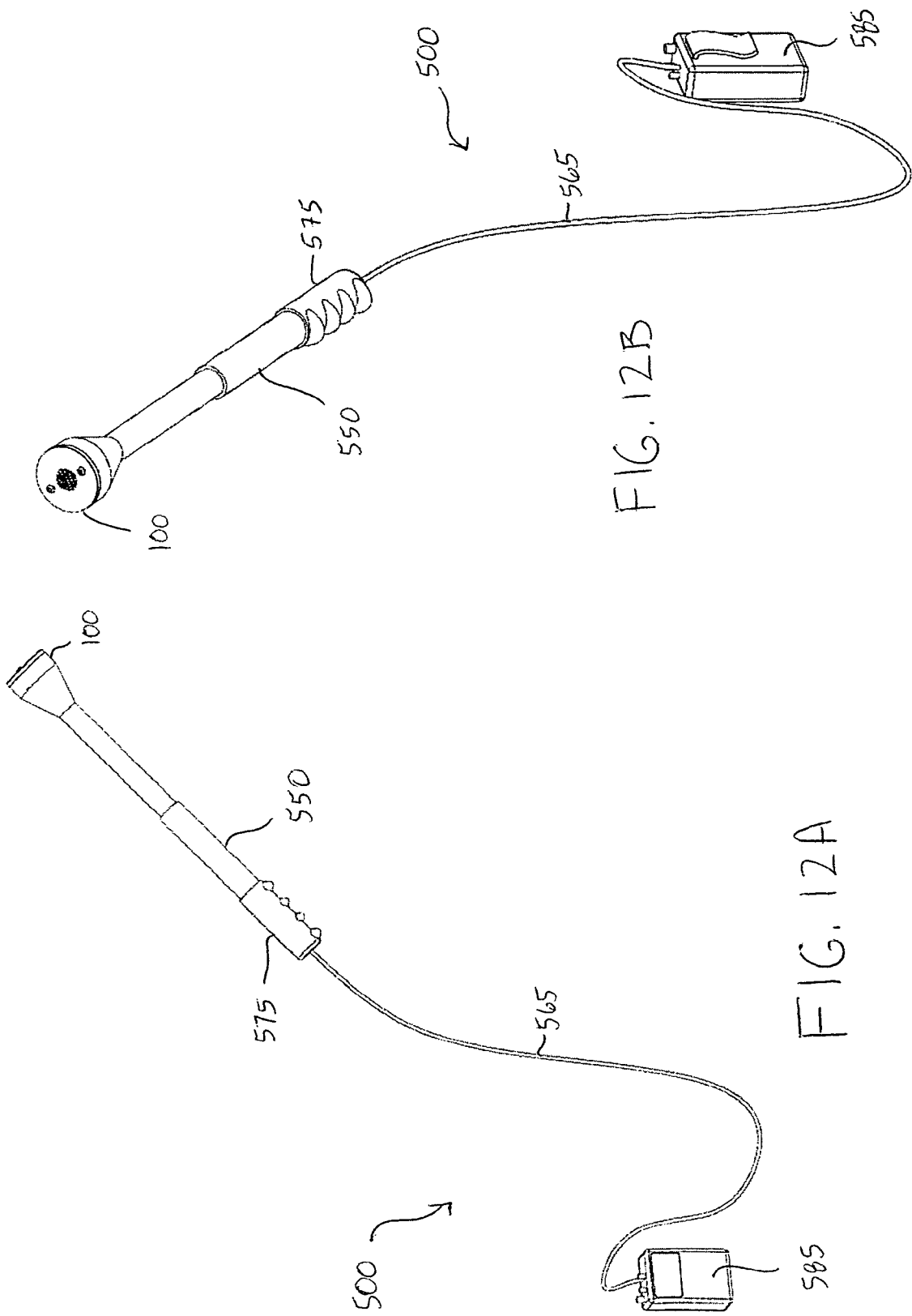

SENSORS AND RELATED DEVICES AND METHODS

BACKGROUND

1. Field

The present invention relates generally to sensors and, more particularly, to sensors that utilize surface acoustic wave (SAW) devices. The present invention also relates to devices that include the present sensors, and to certain methods.

2. Description of Related Art

The use of surface acoustic wave (SAW) devices in apparatuses suited to sensor and detecting the presence of various chemicals is well known. See, for example, the discussion in the background section of U.S. Pat. No. 5,012,668, which patent is incorporated by reference. See also the description of how an array of SAW devices can be used in U.S. Pat. No. 6,321,588, which is incorporated by reference.

SUMMARY

The inventors have identified certain shortcomings with existing or previously-described sensors that use SAW devices. These shortcomings include SAW devices that are arranged such that gas passes over them in sequential fashion; unnecessary surface area between the sensor inlet and the SAW devices; sensors that are bulky; and sensors that are overly complex and, therefore, too expensive and/or prone to failure. Certain of the present devices and methods are designed to address certain of these and other shortcomings.

The present devices and methods include many different features that distinguish them from existing or previously-described sensors. Different embodiments of the present devices and methods include one or more of these features, which are effectively interchangeable between embodiments. Any combination of SAW devices suited to sensing a given chemical may be used consistently with the present sensors. Furthermore, any suitable back-end detecting engine may be used to process signals coming from the SAW devices to serve the function of ultimately ascertaining the identity of chemical(s) that are sensed.

In some embodiments, the present sensors include, consist of, or consist essentially of an inlet structure; a mounting structure that is spaced apart from the inlet structure, the mounting structure having a top surface and an opposing bottom surface; and surface acoustic wave (SAW) devices disposed on the top surface of the mounting structure; where (a) the mounting structure includes openings that extend from the top surface to the bottom surface through which fluid can flow that has first passed over the SAW devices during operation of the sensor, or (b) the mounting structure and SAW devices together define openings through which fluid can flow that has first passed over the SAW devices during operation of the sensor.

In other embodiments, the sensors also include, consist of, or consist essentially of a filter positioned downstream of the inlet structure and upstream of the SAW devices. The filter may be adhesively secured to the inlet structure. The sensors may also include, consist of, or consist essentially of a flow-guiding structure positioned downstream of the filter and upstream of the SAW devices, the flow-guiding structure including flow-guiding openings, at least one of which is positioned directly over a SAW device. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. At least six SAW devices may be disposed on the top surface of the mounting structure. The flow-guiding structure may include, consist of, or consist essentially of at least one flow-guiding opening positioned directly above each SAW device. The sensors may also include, consist of, or consist essentially of a fluid driver positioned downstream of the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of an inlet structure having inlet openings; a mounting structure that is spaced apart from the inlet structure; and surface acoustic wave (SAW) devices connected to the mounting structure; where (a) the mounting structure includes mounting structure openings through which fluid can flow during operation of the sensor, at least one mounting structure opening being positioned adjacent one SAW device, or (b) the mounting structure and SAW devices together define openings through which fluid can flow that has first passed over the SAW devices during operation of the sensor; and where the mounting structure is oriented such that fluid that flows through the inlet openings and toward the SAW devices will impinge substantially perpendicularly on the SAW devices.

In other embodiments, the sensors also include, consist of, or consist essentially of a filter positioned downstream of the inlet structure and upstream of the SAW devices. The filter may be adhesively secured to the inlet structure. The sensors may also include, consist of, or consist essentially of a flow-guiding structure positioned downstream of the filter and upstream of the SAW devices, the flow-guiding structure including flow-guiding openings, at least one of which is positioned directly over a SAW device. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. At least six SAW devices may be connected to the mounting structure. The flow-guiding structure may include, consist of, or consist essentially of at least one flow-guiding opening positioned directly above each SAW device. The sensors may also include, consist of, or consist essentially of a fluid driver positioned downstream of the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of an inlet structure having inlet openings; a mounting structure that is spaced apart from the inlet structure; and surface acoustic wave (SAW) devices connected to the mounting structure; where the mounting structure is oriented such that fluid flowing through the inlet openings and toward the SAW devices will impinge substantially perpendicularly on the SAW devices.

In other embodiments, the sensors may also include, consist of, or consist essentially of a filter positioned downstream of the inlet structure and upstream of the SAW devices. The filter may be adhesively secured to the inlet structure. The sensors may also include, consist of, or consist essentially of a flow-guiding structure positioned downstream of the filter and upstream of the SAW devices, the flow-guiding structure including flow-guiding openings, at least one of which is positioned directly over a SAW device. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. At least six SAW devices may be connected to the mounting structure. The flow-guiding structure may include, consist of, or consist essentially of at least one flow-guiding opening positioned directly above each SAW device. The sensors may also include, consist of, or consist essentially of a fluid driver positioned downstream of the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have has a mass no greater than 100 grams.

In some embodiments, the present sensors include, consist of, or consist essentially of an inlet structure having inlet openings; a mounting structure that is spaced apart from the inlet structure; and surface acoustic wave (SAW) devices connected to the mounting structure; where (a) the mounting structure includes mounting structure openings through which fluid can flow during operation of the sensor, at least one mounting structure opening being positioned adjacent one SAW device, or (b) the mounting structure and SAW devices together define openings through which fluid can flow that has first passed over the SAW devices during operation of the sensor; and where the mounting structure is oriented such that fluid that flows through the inlet openings and toward the SAW devices will flow past the SAW devices in a parallel flow geometry.

In other embodiments, the sensors may also include, consist of, or consist essentially of a filter positioned downstream of the inlet structure and upstream of the SAW devices. The filter may be adhesively secured to the inlet structure. The sensors may also include, consist of, or consist essentially of a flow-guiding structure positioned downstream of the filter and upstream of the SAW devices, the flow-guiding structure including flow-guiding openings, at least one of which is positioned directly over a SAW device. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. At least six SAW devices may be connected to the mounting structure. The flow-guiding structure may include, consist of, or consist essentially of at least one flow-guiding opening positioned directly above each SAW device. The sensors may also include, consist of, or consist essentially of a fluid driver positioned downstream of the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of a top having openings through which fluid initially flows into the sensor; a mounting structure spaced apart from the top, the mounting structure having (a) a mounting structure top surface that is parallel to the top, and (b) a mounting structure bottom surface; and surface acoustic wave (SAW) devices connected to the mounting structure top surface; where the mounting structure includes openings that extend from the mounting structure top surface to the mounting structure bottom surface through which fluid that passes over the SAW devices can flow during operation of the sensor.

In other embodiments, the sensors may also include, consist of, or consist essentially of a filter positioned downstream of the top and upstream of the SAW devices. The filter may be adhesively secured to material forming the top. The sensors may also include, consist of, or consist essentially of a flow-guiding structure positioned downstream of the filter and upstream of the SAW devices, the flow-guiding structure including flow-guiding openings, at least one of which is positioned directly over a SAW device. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. At least six SAW devices may be disposed on the mounting structure top surface. The flow-guiding structure may include, consist of, or consist essentially of at least one flow-guiding opening positioned directly above each SAW device. The sensors may also include, consist of, or consist essentially of a fluid driver positioned downstream of the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of a top having openings and an undersurface; a mounting structure spaced apart from the top, the mounting structure having a mounting structure top surface that is parallel to the top and that faces in the direction of the undersurface; surface acoustic wave (SAW) devices disposed on the mounting structure top surface; a filter positioned underneath, and secured adhesively to, the top; a flow-guiding structure positioned between the filter and the SAW devices, the flow-guiding structure including flow-guiding openings, at least one of which is positioned directly above a SAW device; openings in the mounting structure through which fluid can flow after passing over the SAW devices during operation of the sensor; and a fluid driver positioned downstream of the mounting structure.

In other embodiments, at least six SAW devices may be disposed on the mounting structure top surface. The flow-guiding structure may include, consist of, or consist essentially of at least one flow-guiding opening positioned directly above each SAW device. The filter may comprise, consist of, or consist essentially of a gas-permeable membrane that is chemically inert. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of a top having a top surface, a bottom surface, and openings positioned in the top that extend from the top surface to the bottom surface; surface acoustic wave (SAW) devices connected to a mounting structure that is spaced apart from the top, the mounting structure including openings through which fluid can flow after passing over the SAW devices; a filter positioned downstream of the top; a flow-guiding structure positioned between the filter and the SAW devices, the flow-guiding structure including flow-guiding openings, at least one of which is positioned directly over a SAW device; and a fluid driver positioned downstream of the mounting structure, the fluid driver being configured to help draw fluid in a direction that is substantially straight through (a) the filter, (b) the flow-guiding openings, and (c) the openings in the mounting structure; where the mounting structure is oriented such that fluid flowing in the direction will (a) impinge substantially perpendicularly on the SAW devices, and (b) flow past the SAW devices in a parallel flow geometry.

In other embodiments, at least six SAW devices may be connected to the mounting structure. The flow-guiding structure may include, consist of, or consist essentially of at least one flow-guiding opening positioned directly above each SAW device. The filter may comprise, consist of, or consist essentially of a gas-permeable membrane that is chemically inert. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of a top having a top surface, a bottom surface, and openings positioned in the top that extend from the top surface to the bottom surface; surface acoustic wave (SAW) devices connected to a mounting structure that is spaced apart from the top, the mounting structure including openings through which fluid can flow after passing over the SAW devices; a filter positioned downstream of the top; a flow-guiding structure positioned between the filter and the SAW devices, the flow-guiding structure including flow-guiding openings, at least one of which is positioned directly over a SAW device; and a fluid driver positioned downstream of the mounting structure; where the mounting structure is oriented such that fluid flowing in a direction that is substantially straight through (a) the filter, (b) the flow-guiding openings, and (c) the openings in the mounting structure will impinge substantially perpendicularly on the SAW devices and flow past the SAW devices in a parallel flow geometry.

In other embodiments, at least six SAW devices may be connected to the mounting structure. The flow-guiding structure may include, consist of, or consist essentially of at least one flow-guiding opening positioned directly above each SAW device. The filter may comprise, consist of, or consist essentially of a gas-permeable membrane that is chemically inert. The flow-guiding structure may include, consist of, or consist essentially of a flow-guiding structure top surface having a recessed portion from which flow-guiding openings extend and into which fluid flows after first passing through the filter, the recessed portion being defined at least in part by a recessed surface that is below the flow-guiding structure top surface. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present sensors include, consist of, or consist essentially of an inlet structure; a permeable and chemically-inert membrane positioned downstream of the inlet structure; and surface acoustic wave (SAW) devices connected to a mounting structure that is spaced apart from the membrane, the mounting structure including openings through which fluid can flow during operation of the sensor; where the mounting structure is oriented such that fluid flowing in a direction that runs substantially straight from the inlet structure through openings in the mounting structure will (a) impinge substantially perpendicularly on the SAW devices, and (b) flow past the SAW devices in a parallel flow geometry.

In other embodiments, the sensors may also include, consist of, or consist essentially of a flow-guiding structure positioned between the membrane and the SAW devices, the flow-guiding structure including flow-guiding openings, at least one of which is positioned directly over a SAW device. At least six SAW devices may be connected to the mounting structure. The flow-guiding structure may include, consist of, or consist essentially of at least one flow-guiding opening positioned directly above each SAW device. The sensors may also include, consist of, or consist essentially of a fluid driver positioned downstream of the mounting structure, the fluid driver being no more than 0.1 inches from the mounting structure. The sensors may also include, consist of, or consist essentially of an orifice plate positioned downstream of the mounting structure and upstream of the fluid driver, the orifice plate including an opening through which fluid flows after exiting openings in the mounting structure. The sensors may have a size no greater than 2 cubic inches. The sensors may have a mass no greater than 100 grams.

In some embodiments, the present methods include, consist of, or consist essentially of (a) causing fluid to enter a sensor through openings in a top of the sensor; (b) causing at least some of the fluid to pass through a permeable membrane that is positioned downstream of the top; (c) causing at least some of the fluid to flow through openings in a flow-guiding structure positioned downstream of the permeable membrane; and (d) causing at least some of the fluid to (i) impinge substantially perpendicularly on surface acoustic wave (SAW) devices that are connected to a mounting structure that is positioned downstream of the flow-guiding structure, and (ii) pass over the SAW devices in a parallel flow geometry.

In other embodiments, a fluid driver positioned downstream of the mounting structure helps achieve at least some of the (b) causing, the (c) causing, or the (d) causing.

In some embodiments, the present devices include, consist of, or consist essentially of a sensor having an inlet structure having inlet openings through which fluid that is first entering the sensor flows; a mounting structure that is spaced apart from the inlet, the mounting structure having a mounting structure top surface; and surface acoustic wave (SAW) devices disposed on the mounting structure top surface; where (a) the mounting structure includes openings through which fluid can flow that has first passed over the SAW devices during operation of the sensor, or (b) the mounting structure and SAW devices together define openings through which fluid can flow that has first passed over the SAW devices during operation of the sensor.

In other embodiments, the device also includes, consists of, or consists essentially of a micro air vehicle attached to the sensor; an arm connected to the sensor; or a rugged package to which the sensor is connected. The arm may be a telescoping arm having a variable effective length.

Other embodiments of the present sensors, methods and devices are possible.

BRIEF DESCRIPTION OF THE DRAWINGS

The following drawings illustrate by way of example and not limitation. Identical reference numerals do not necessarily indicate an identical structure. Rather, the same reference numeral may be used to indicate a similar feature or a feature with similar functionality. Every feature of each embodiment is not always labeled in every figure in which that embodiment appears, in order to keep the figures clear.

FIGS. 9B and 9C is a perspective view and a partial top view, respectively, of another embodiment of the present mounting structures, where the mounting structure and SAW devices together form openings through which fluid can flow after first passing over the SAW devices.

FIG. 11A shows one embodiment of the present devices that includes a micro air vehicle (MAV) and one of the present sensors.

FIG. 11B shows another embodiment of the present devices that includes a micro air vehicle (MAV) and one of the present sensors.

FIGS. 12A and 12B show different views of one embodiment of the present devices that includes a sensor connected to a telescoping shaft.

DESCRIPTION OF ILLUSTRATIVE EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device, sensor or method that "comprises," "has," "contains," or "includes" one or more elements possesses those one or more elements, but is not limited to possessing only those one or more elements or steps. Likewise, an element of a device, sensor or method that "comprises," "has," "contains," or "includes" one or more features possesses those one or more features, but is not limited to possessing only those one or more features. Furthermore, a structure that is configured in a certain way must be configured in at least that way, but also may be configured in a way or ways that are not specified.

The terms "a" and "an" are defined as one or more than one unless this disclosure explicitly requires otherwise. The terms "substantially" and "about" are defined as at least close to (and includes) a given value or state (preferably within 10% of, more preferably within 1% of, and most preferably within 0.1% of).

Figure 1:
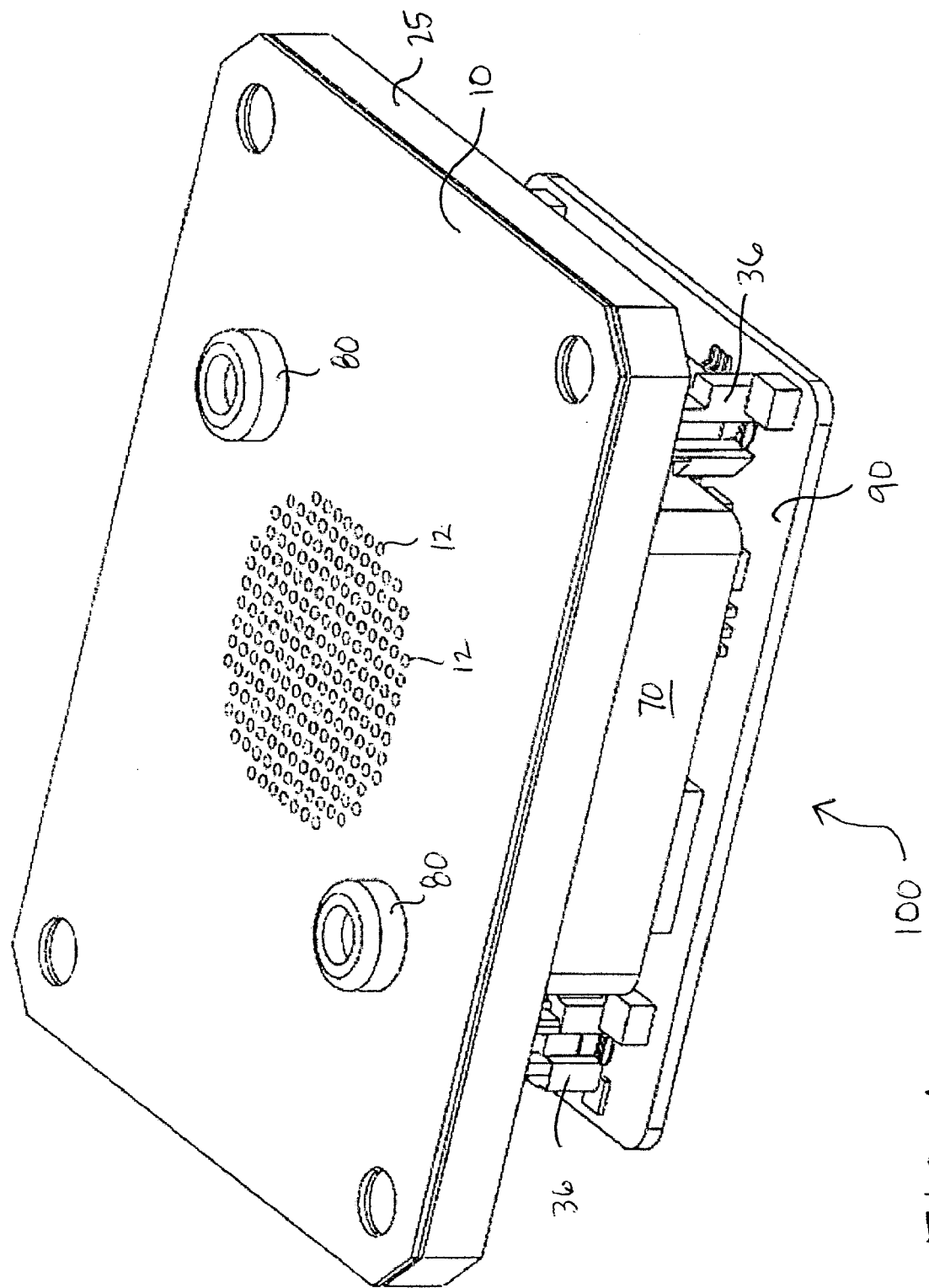
FIG. 1 is a perspective view of one embodiment of the present sensors.

An exemplary embodiment of the present sensors appears in a perspective view in FIG. 1. Sensor 100 includes, broadly, an inlet structure 10 and a mounting structure 40 (visible in FIGS. 2 and 5) to which surface acoustic wave (SAW) devices 30 are connected. Mounting structure 40 includes openings 42 (e.g., mounting structure openings) through which gas (or, more generally, fluid) that is flowing through sensor 100 can flow after the fluid first passes over SAW devices 30. Inlet structure 10 includes inlet openings 12 through which fluid that is first entering sensor 100 flows.

Figure 5:
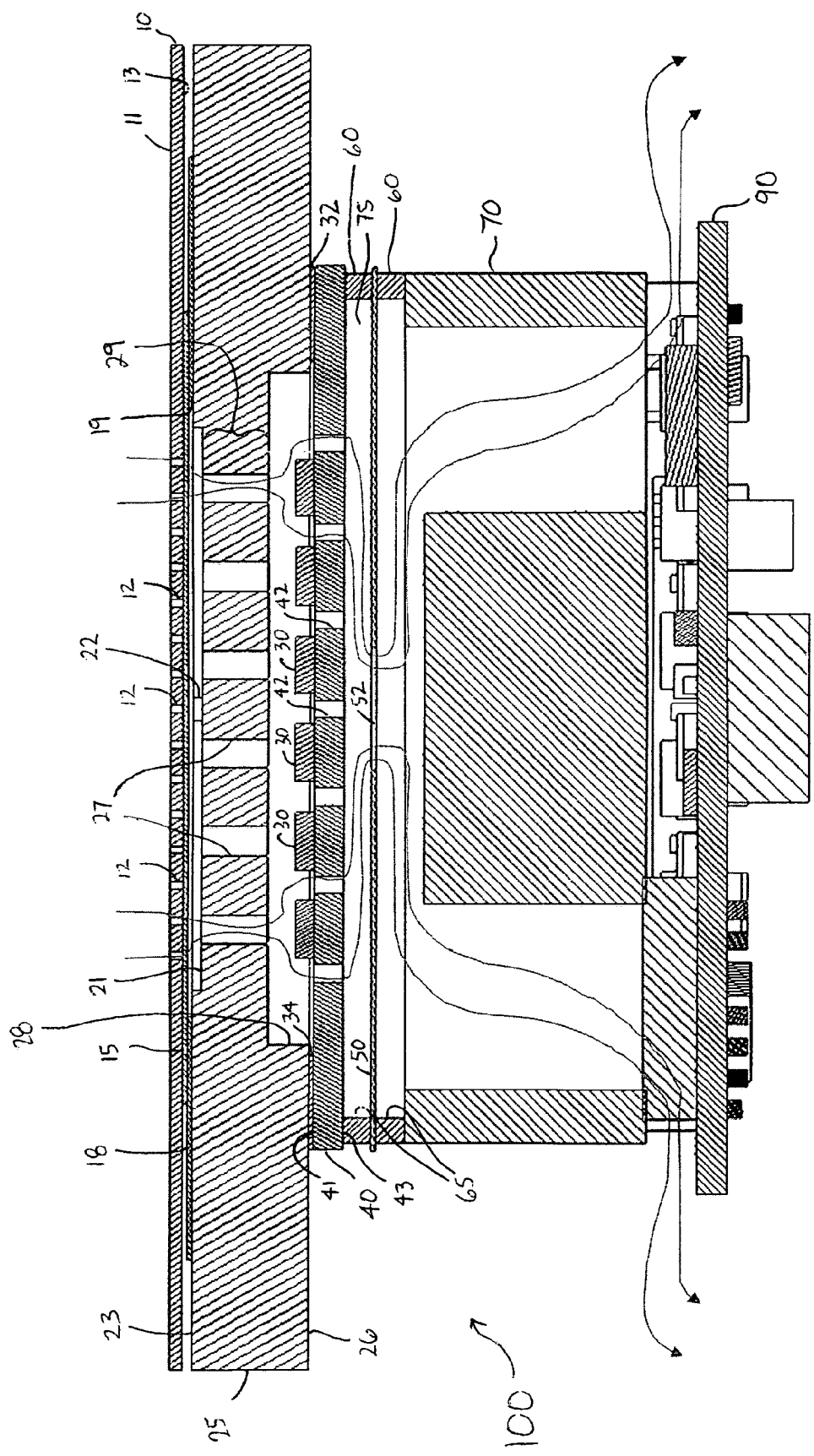
FIG. 5 is a cross-sectional view of the sensor shown in FIGS. 1 and 2, taken at a location that shows how fluid can flow through the sensor.

As shown in other figures, especially FIG. 5, inlet structure 10 and mounting structure 40 are substantially parallel (and, in this embodiment, parallel) to each other and are substantially aligned (and, in this embodiment, aligned), such that fluid that flows from inlet structure 10 toward mounting structure 40 and into SAW devices 30 is moving in substantially one, straight direction. By contrast, the fluid that flows through gas admission chamber 5 and then makes a right-hand turn to flow radially across modules 2 of U.S. Pat. No. 5,817,922 (which is incorporated by reference) is not flowing in substantially one, straight direction. The substantially aligned arrangement of inlet structure 10 and mounting structure 40 is advantageous because, generally, the fewer turns the fluid flowing through sensor 100 toward SAW devices 30 must take in order to reach SAW devices 30, the less surface area that fluid is exposed to, and the less diluted the concentration of target material in that fluid is likely to become. The arrangement of inlet structure 10 relative to mounting structure 40 is one that allows fluid that flows through inlet openings 12 and past any components positioned between inlet structure 10 and SAW devices 30 to impinge substantially perpendicularly on SAW devices 30.

Figure 2:
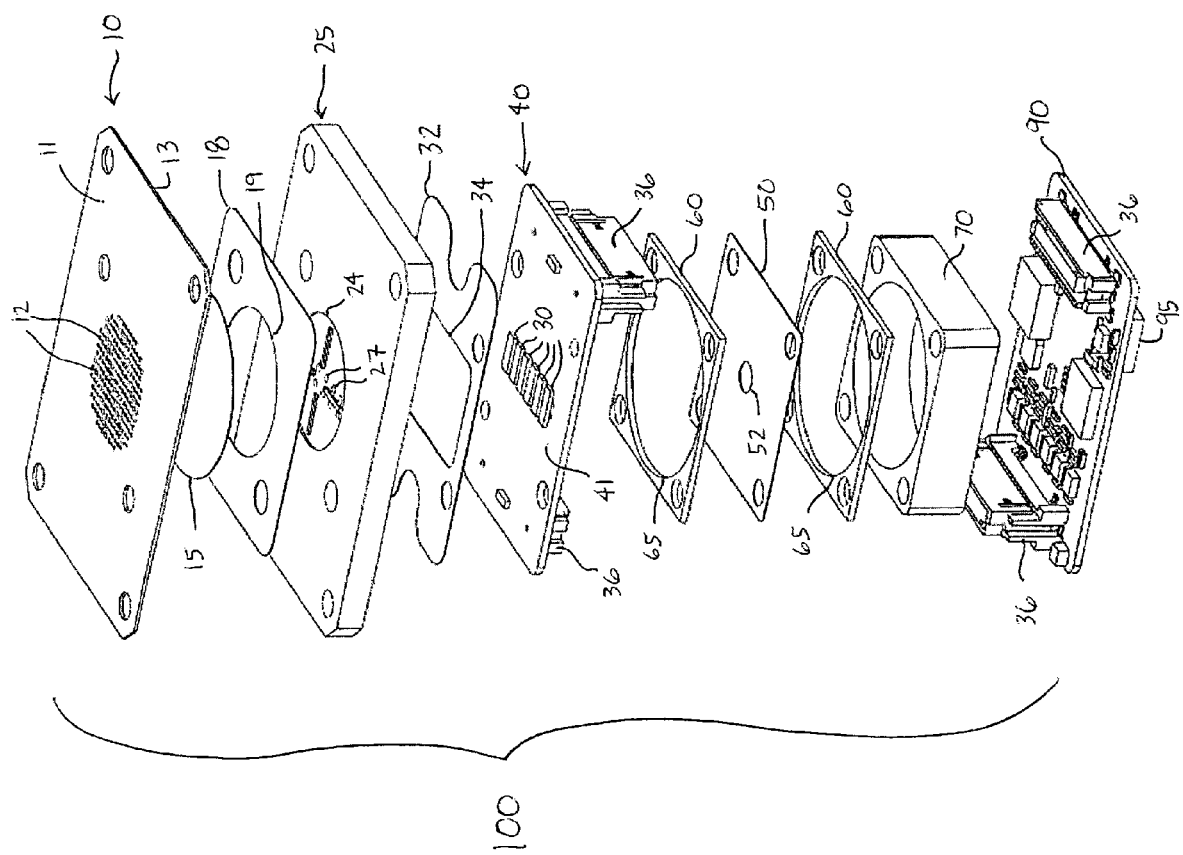
FIG. 2 is an exploded view (in perspective) of the sensor shown in FIG. 1.

FIG. 2 shows an exploded view of sensor 100, and reveals components that may be used to construct one of the present sensors. Inlet structure 10, which can also be referred to as a "top" or "top structure," is shown as a substantially flat (and, in this embodiment, flat) plate. Stainless steel 302 is one suitable material from which inlet structure 10 may be constructed. Other materials, such as synthetic, non-metal materials (e.g., unfilled polyamide 612 or 66 (e.g., NYLON brand)) may be used in other embodiments.

Inlet structure 10 includes a top surface 11 and an opposing, substantially-parallel (and, in this embodiment, parallel) bottom surface 13 and inlet openings 12 that extend from top surface 11 to bottom surface 13 and through which fluid initially entering sensor 100 flows. Inlet openings 12 may be formed in inlet structure 10 by removing material from inlet structure 10 (e.g., by stamping, drilling, cutting, etc.) after inlet structure 10 is formed. Inlet opening 12 may be substantially centered in inlet structure 10, and may have an outer configuration of any suitable type (e.g., substantially circular, as in this embodiment). Inlet structure 10 may have a thickness of 0.015 inches, although other sizes may be used.

Filter 15 is positioned downstream of inlet structure 10 and upstream of mounting structure 20 and SAW devices 30. A gas-permeable, chemically-inert membrane may be used for filter 15. The membrane may be micro-porous, and may be made of any suitable material, such as expanded polytetrafluoroethylene (PTFE). One suitable brand of expanded PTFE is W. L. Gore & Associates, Inc.'s Gore-Tex® expanded PTFE, part no. VE0002BAE. The fluid driver that may be used with sensor 100 (discussed below in more detail) and filter 15 (when a filter is used) may be considered together to achieve a size for each that is best suited to a given application of the sensor in question.

Filter 15 may abut, or be positioned very close to, inlet structure 10. One way to achieve an abutting relationship between the two involves simply connecting them together with fasteners, as discussed in more detail below, such that they are touching each other when the sensor is assembled. Although one may effectively exist, no seal between filter 15 and inlet 10 is needed in such an embodiment. Such a relationship is shown in FIG. 5. Another way to achieve an abutting relationship between the two is to adhesively secure filter 15 to inlet structure 10 in any suitable manner, such as by providing filter 15 with an adhesive backing that could be used to adhesively secure it to inlet structure 10.

Together, inlet structure 10 and filter 15 filter out large particles from the fluid stream entering sensor 100, with inlet openings 12 filtering out the bigger particles. Because inlet structure 10 can be rigid, it also serves to protect filter 15 from damage.

Sensor 100 may also include a flow-guiding structure 25 that is positioned downstream of inlet structure 10 and filter 15, but upstream of SAW devices 30 and mounting structure 40. Flow-guiding structure 25 may be a substantially flat (and, in this embodiment, flat) plate that is 0.130 inches thick, although other thicknesses may be used. Unfilled polyamide 612 or 66, which is low absorption material, may be used as the material from which flow-guiding structure 25 is formed, although other suitable materials may also be used.

In some embodiments, it is desirable to create a seal between flow-guiding structure 25 and filter 15. One way to achieve a suitable seal involves the use of a gasket 18, which can be a piece of low-out gassing tape, such as 3M™ Adhesive Transfer Tape 467MP that is 0.005 inches thick without its backing sheets, or release liners, and that may be double-sided. As FIG. 2 shows, filter 15 may be cut to have any suitable shape, such as circular, and may have a larger diameter than the diameter of the pattern formed by inlet openings 12. Gasket 18 may be provided with a flow opening 19 that is smaller than the diameter of filter 15, but at least as large as the pattern formed by inlet openings 12. Gasket 18 may have adhesive on both of its surfaces (its top and bottom surfaces). As a result, gasket 18 may adhesively secure filter 15 to flow-guiding structure 25 as shown in FIG. 5. In this embodiment, gasket 18 may adhesively secure filter 15 to inlet structure 10.

Figure 3:
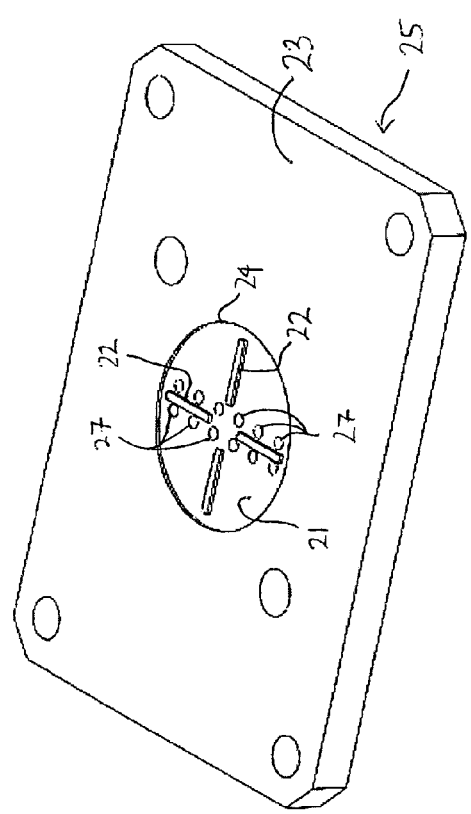
FIG. 3 is a top perspective view of one of the present flow-guiding structures.
Figure 4:
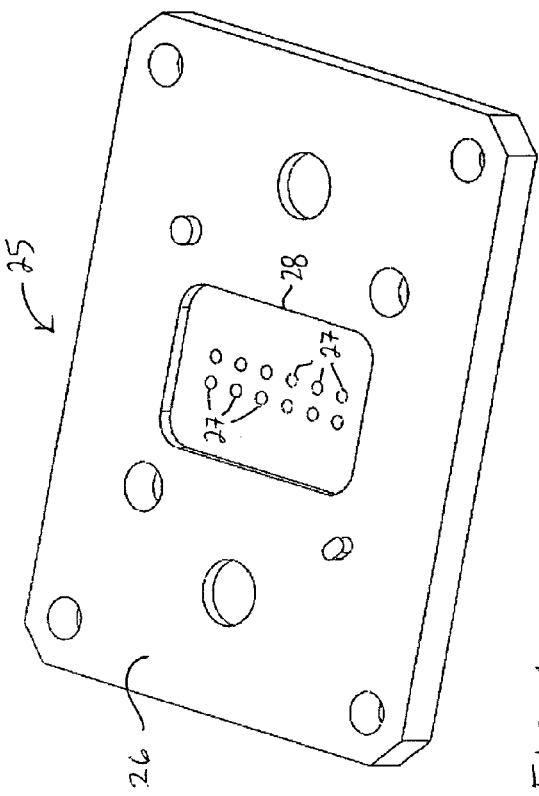
FIG. 4 is a bottom perspective view of the flow-guiding structure shown in FIG. 3.

Flow-guiding structure 25 may be configured to direct fluid flowing through sensor 100 to flow directly into one or more of SAW devices 30. This configuration may be achieved, at least in part, with flow-guiding openings 27 provided in flow-guiding structure 25. FIGS. 3 and 4 show flow-guiding structure 25 in more detail. These figures show that flow-guiding structure includes a top surface 23 (e.g., a flow-guiding structure top surface) and an opposing, substantially-parallel (and, in this embodiment, parallel) bottom surface 26. Top surface 23 has a recessed portion 24 that, in this embodiment, is circular-shaped. Recessed portion 24 is roughly (e.g., substantially) the same shape as the pattern formed by inlet openings 12, and is slightly smaller than flow opening 19 in gasket 18. Recessed portion 24 is defined at least in part by a recessed surface 21 that is parallel to, and below, top surface 23. The distance between top surface 23 and recessed surface 21 may be 0.012 inches, although other distances are possible.

Filter supports 22 extend upwardly from recessed surface 21, and serve to hold up (or prop up) filter 15, to the extent that filter 15 tends to dip or sag as fluid flows through it or is drawn through it. Instead of using filter supports 22 having the shape of elongated spines, a series of bumps or pin-shaped protrusions may also be used; moreover, any suitable shape may be used for filter supports 22 (further, only one filter support 22 may be used in some embodiments) provided that shape helps to prop up filter 15 during use of the sensor.

The space created by recessed portion 24 as shown in FIG. 5 creates a pocket into which fluid can flow that has first passed through filter 15. In some embodiments, this recessed portion can be dispensed with, but then the only fluid flowing through flow-guiding openings 27 is the fluid coming through the filter directly above those openings. The pocket created using recessed portion 24 is a larger area from which filtered fluid may be drawn through flow-guiding openings 27. As a result, the pocket increases the effective filter area of the portions of filter 15 through which fluid flows, thus either lessening the energy required to power the fluid driver or increasing the fluid flow rate for a given fluid driver head capacity.

Bottom surface 26 of flow-guiding structure 25 has a recessed portion 28 that, in this embodiment, is rectangular-shaped (with rounded corners). Recessed portion 28 may be 0.045 inches deep, although other depths are possible. As FIG. 5 shows, at least a portion of recessed portion 28 is directly beneath a portion of recessed portion 24. As a result, the portion of flow-guiding structure 25 in which flow-guiding openings 27 are positioned is thinner than the remainder of flow-guiding structure 25, and the fluid flowing through flow-guiding openings 27 is exposed to less surface area (of flow-guiding structure 25) than it would be exposed to if it were flowing through the entire thickness of flow-guiding structure 25. This thinner portion is designated as reduced thickness portion 29 in FIG. 5. Recessed portion 28 also functions to position the bottoms of flow-guiding openings 27 closer to the tops of SAW devices 30. Flow-guiding openings 27 may be characterized as non-gas chromatography columns or as non-nozzle openings, and the space created by recessed portion 28, which is spaced into which fluid can flow after passing through flow-guiding openings 27 but before impinging substantially perpendicularly on SAW devices 30, may be characterized as open, non-columned space. Furthermore, flow-guiding structure 25 may be characterized as a non-nozzle flow-guiding structure, in contrast to the nozzle through which fluid flows prior to impinging absorption area 24 in U.S. Pat. No. 5,239,715 (see FIG. 2), which is incorporated by reference.

At least one flow-guiding opening 27 in flow-guiding structure 25 may be positioned directly over a SAW device 30. In the embodiment shown, one flow-guiding opening 27 is positioned over (e.g., directly over) each SAW device 30. More specifically, two flow-guiding openings 27 are positioned over (e.g., directly over) each SAW device 30. In other embodiments, more than two flow-guiding openings may be positioned over one or more of the SAW devices used.

Another gasket—gasket 32—may be placed between flow-guiding structure 25 and mounting structure 25. Gasket 32 may be made from the same material as gasket 18, and may have the same thickness as gasket 18, although a gasket having any suitable thickness may be used. Gasket 32 is provided with a flow opening 34 that has a similar shape to that of recessed portion 28 of flow-guiding structure 25, but that is slightly larger in perimeter, as shown in FIG. 5. Gasket 32 is sandwiched between (and thus in contact with, and the only thing separating) flow-guiding structure 25 (and, more specifically, bottom surface 26 of flow-guiding structure 25) and mounting structure 40 (and, more specifically, top surface 41 of mounting structure 40). When made of a double-sided adhesive material, gasket 32 also adhesively connects flow-guiding structure 25 to mounting structure 40. Gasket 32 may alternatively be made without adhesive on either its top or bottom sides. Regardless of the seal from which it is made, gasket 32 may form a seal between flow-guiding structure 25 and mounting structure 40 that prevents fluid from escaping between them as it flows through them. An O-ring could be used in place of gasket 32, and a groove for the O-ring provided in an appropriate location in the bottom surface of flow-guiding structure 25.

Figure 6:
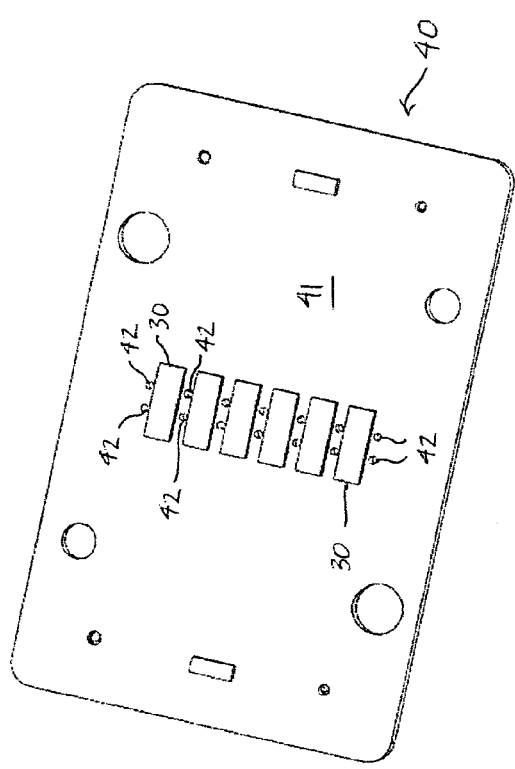
FIG. 6 is a top perspective view of one of the present mounting structures.
Figure 7:
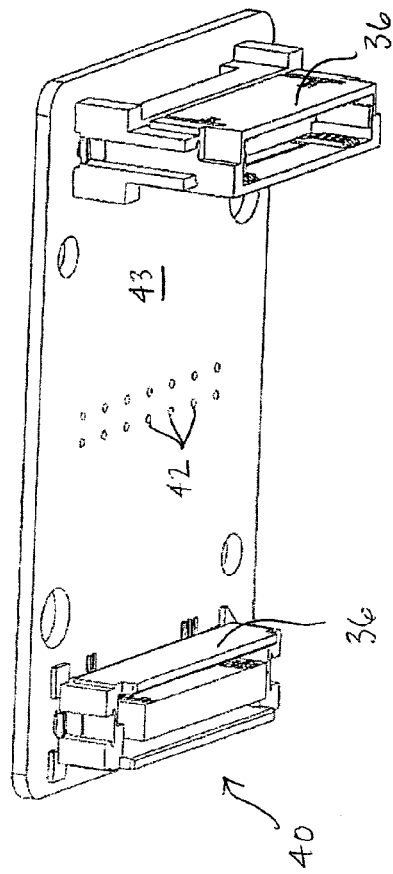
FIG. 7 is a bottom perspective view of the mounting structure shown in FIG. 6.

Mounting structure 40 is positioned downstream of, and is spaced apart from, inlet structure 10. A suitable material for mounting structure 40 is FR4 fiberglass. FIGS. 6 and 7 show mounting structure 40 in more detail. Mounting structure 40 includes a top surface 41, and an opposing, substantially-parallel (and, in this embodiment, parallel) bottom surface 43. The portions of top surface 41 of mounting structure 40 that are exposed to a sample fluid stream may be gold-plated. SAW devices 30 are connected to mounting structure 40, and that connection may be achieved in any suitable manner known in the art. SAW devices 30 may be described, in this embodiment, as being disposed on top surface 41 of mounting structure 40.

While SAW devices 30 are shown arranged in a straight line across top surface 41, they may be positioned in other arrangements that may be better suited to a given application for sensor 100. Furthermore, any suitable number of SAW devices may be used (e.g. 2, 3, 4, 5, 6, 7, 8, or more), although 6 are shown in FIGS. 2, 5 and 6. Any type of SAW device suited to a given application may be used consistently with the present sensors, including those with a piezoelectric quartz substrate that has been coated with a chemically-sensitive film (e.g., a polymer), although such a coating need not be used.

As shown in FIG. 6, openings 42 may extend through mounting structure 40 from top surface 41 to bottom surface 43. The openings may be positioned adjacent to, or beside, one or more of the SAW devices 30. Fluid that flows over a given SAW device 30 can then flow through one or more openings 42. As FIG. 6 shows, two openings 42 may be positioned on each side of (and adjacent to) each SAW device 30. Even more specifically, FIG. 6 shows that there are two openings 42 positioned between each pair of SAW device 30. Openings 42 allow for fluid to flow past SAW devices 30 in a parallel flow geometry, meaning that each SAW device is exposed to a sample fluid stream that has not been diluted by other SAW devices, as is the case in sensors that rely on fluid flow across a series of SAW devices, where the concentration of a target chemical could be diluted as it passes over each successive SAW device. In a preferred embodiment, a sensor that includes a mounting structure that is oriented and configured for fluid to flow past SAW devices in a parallel flow geometry is a sensor in which each SAW device is substantially simultaneously (and, in an even more preferred embodiment, simultaneously) exposed to a substantially equivalent (and in an even more preferred embodiment, equivalent) flow rate and volume of fluid. Besides reducing the depletion of target chemicals in a sample fluid stream, a parallel flow geometry also may reduce the transient response time of the SAW device (from response times of SAW devices arranged such that fluid flows across them in serial fashion).

Figure 8:
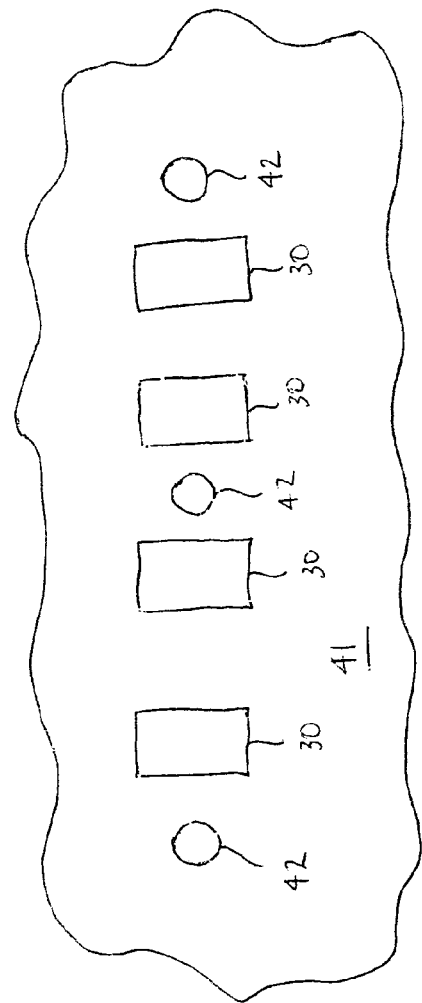
FIG. 8 is a partial top view of one embodiment of an arrangement of openings in one of the present mounting structures that allows fluid to flow past SAW devices in a parallel flow geometry.

Other configurations of openings 42 that allow for fluid to flow past SAW devices 30 in a parallel flow geometry are possible. One is shown in FIG. 8.

Figure 9A:
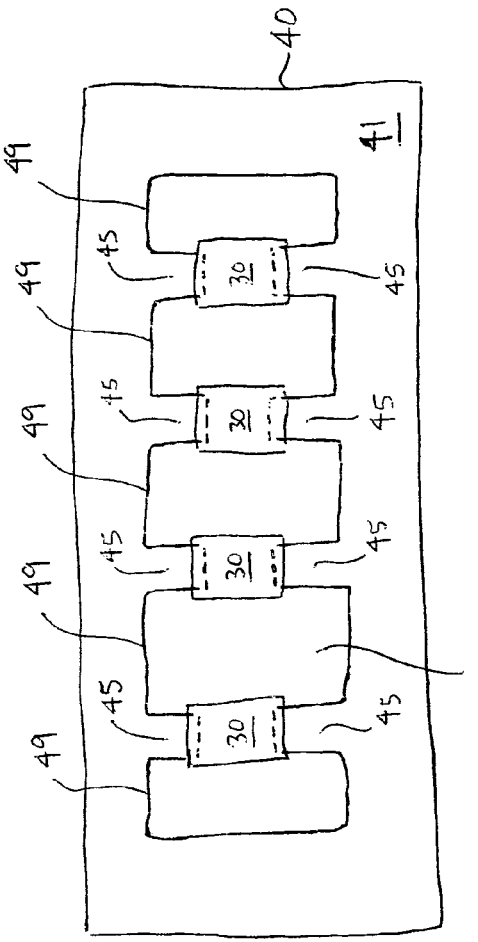
FIG. 9A is a top view of one embodiment of the present mounting structures, where the mounting structure and SAW devices together form openings through which fluid can flow after first passing over the SAW devices.

Furthermore, instead of openings positioned in, and running through the thickness of, mounting structure 40, the mounting structure could be configured such the mounting structure together with the SAW devices defines openings through which fluid can flow that has first passed over the SAW devices during operation of the sensor. FIG. 9A shows one such embodiment. In this embodiment, SAW devices 30 are connected to mounting structure 40, and also are disposed on top surface 41 of mounting structure 40. The embodiment of mounting structure 40 shown in FIG. 9A includes SAW device-support projections 45. In this embodiment, two projections are spaced apart from and extend toward each other at spaced intervals, for a total of four pairs of SAW device-support projections 45. One SAW device 30 is connected to, and disposed on, each pair of projections 45. Projections 45 define, in part, a single flow opening 47. This embodiment of mounting structure 40 (and, more particularly, the SAW-device support projections) and the SAW devices 30 together define openings 49 through which fluid can flow that has first passed over SAW devices 30 during operation of sensor 100. Other configurations of projections 45, and thus openings 49, are possible.

Another version of a mounting structure configured such the mounting structure together with the SAW devices defines openings through which fluid can flow that has first passed over the SAW devices during operation of the sensor is shown in FIGS. 9B and 9C. In this embodiment, a slot 44 is provided in mounting structure 40. SAW devices 30 are each disposed on (and, in this embodiment, connected to) a substrate 46 (e.g., an alumina substrate) that is reflowed onto the board that comprises mounting structure 40. This embodiment of mounting structure 40 and the SAW devices 30 together define openings 49 through which fluid can flow that has first passed over SAW devices 30 during operation of sensor 100. This embodiment may result in increased manufacturing yields over other embodiments that lack the use of a substrate 46 on which a SAW device 30 may be disposed because faulty SAW devices can be identified in sub-assemblies before being soldered (or otherwise connected) to mounting structure 40.

It is possible for sensor 100 to include a reference SAW device, but for that reference SAW device not to be disposed on (or otherwise connected to) mounting structure 40. For example, a reference SAW device may be positioned in a standard SAW package 95 that is connected to the bottom (or top) of SAW driver board 90. Thus, such embodiments of the present sensors may be characterized as sensors that include a reference SAW device that is not connected to the same structure (e.g., mounting structure 40) to which the other SAW devices are connected. Such embodiments of the present sensors also may be characterized as sensors that include a reference SAW device that is not disposed on the same surface (e.g., mounting structure top surface 41) on which the other SAW devices are disposed.

Connectors 36 (which could be standard Molex® connectors) are connected to mounting structure 40 (in any suitable manner known in the art), and extend away from bottom surface 43. These connectors are electrically coupled (via, e.g., the gold plating) to the input and output transducers of the SAW devices.

Positioned downstream of mounting structure 40 and fluid driver 70 (discussed below in more detail) is orifice plate 50. Orifice plate 50 includes an opening 52 through which fluid flows after exiting one or more of the openings 42 in mounting structure 40 or openings 49 defined by mounting structure 40 and SAW devices 30. Orifice plate 50 may be made from any suitable material, may be rigid, and may be substantially flat (and, in this embodiment, flat). One suitable material is stainless steel 302, and it may have a thickness of 0.005 inches.

Spacers 60 may be used to separate orifice plate from mounting structure 40 and from fluid driver 70. Thus, the top spacer 60 is in contact with mounting structure 40 on one side, and orifice plate 50 on the other. Similarly, the bottom spacer is in contact with orifice plate 50 on one side, and fluid driver 70 on the other. Each spacer 60 may have a flow opening 65 through which fluid can flow. Spacers 60 may be made from non-conductive, rigid material, such as unfilled polyamide 612 or 66. It is generally not advisable to use a material as pliable as rubber for spacers 60. Spacers 60 may be 0.032 inches thick (although other thicknesses are possible), and may be substantially flat (and, in this embodiment, flat).

Orifice plate 50, and more particularly opening 52 in orifice plate 50, functions to reduce the turbulence of the fluid that has flowed through either openings 42 or 49. When fluid driver 70 comprises an axial fan having a hub diameter of 0.575 inches, the inventors have found that opening 52 having a diameter of 0.150 inches works well in this regard. In embodiments where a fluid driver is positioned as shown in the figures but orifice plate 50 is not used, spacing the bottom surface 43 of mounting structure 40 too close to the top of fluid driver 70 may tend to create a potentially-detrimental amount of turbulence below the opening or openings 42/49 that are positioned directly above the blades of the fluid driver 70 (thus, the outermost opening or openings 42/49 may be affected). Flow through that opening or those openings may, as a result, become more restricted than flow through the more centrally-oriented opening/openings 42/49 that are positioned above other parts of the fluid driver than the blades. Furthermore, regardless of whether an orifice plate is used, flow through the centermost openings 42/49 will also become increasingly restricted as the spacing between the hub of fluid driver 70 (in those instances when a fluid driver is positioned as shown in the figures) and bottom surface 43 approaches zero.

The inventors have discovered that by using the orifice plate 50 having the exemplary thickness listed above with opening 52 having the exemplary size listed above, and spacing orifice plate 50 apart from both the bottom surface 43 of mounting structure 40 and from the top surface of fluid driver 70 using a spacer 60 having the exemplary thickness reported above, a pocket—designated generally as 75 in FIG. 5—is created that is not subject to the turbulence, or shearing effects, of the fluid driver blades. As a result, fluid flows more evenly through openings 42/49 and toward fluid driver 70.

Fluid driver 70 is positioned downstream of orifice plate 50 and mounting structure 40. Any suitably-sized fluid driver may be used. The fluid driver may be a miniature PC fan, a miniature piezo pump, or the like. One suitable style of fan for fluid driver 70 is a SUNON MagLev fan KDE0502PEB1-8, DC5V-0.8 W (although 0.3 W or 0.5 W may be used instead), which is about 6 millimeters thick. As the exemplary fluid flow arrows in FIG. 5 show, fluid driver 70 may be characterized as a flow-through fluid driver (e.g., an axial fan) because fluid can actually flow through the fluid driver past its blades along a path that is parallel with the axis around which the blades that drive the fluid rotate. The flow rate that can be achieved using fluid driver 70 should be considered in view of the pressure drop across the components (e.g., inlet structure 10, filter 15, flow-guiding structure 25) that are upstream of the SAW devices 30 to arrive at a fluid driver that moves fluid at a desired flow rate across SAW devices 30. The use of the components described above having the exemplary dimensions listed above yields a flow rate of about 20 milliliters per minute across SAW devices 30, and, more specifically, yields a flow rate of about 3 ⅓ milliliters per minute across each SAW device 30.

Fluid driver 70 is provided with two or more fastener openings (not numbered) at its corners into which fasteners may be extended. Inlet structure 10, gasket 18, flow-guiding structure 25, mounting structure 40, spacers 60, and orifice plate 50 also are each provided with two or more openings that are aligned with the fastener openings in fluid driver 70, such that any suitable fastener (e.g., plastic screws, such as PLASTITE® screws) may be used to connect all those components to fluid driver 70. Fasteners 80 are shown in FIG. 1 as performing this function.

As shown in the figures, fluid driver 70 may be oriented substantially parallel (and, in the embodiment shown, parallel) to mounting structure 40, flow-guiding structure 25 and inlet structure 10, and may also be substantially aligned (and, in the embodiment shown, aligned) with these same structures.

Mounting structure 40, and thus the balance of the embodiment of sensor 100 shown in FIG. 2 (including fluid driver 70), may be connected to SAW driver board 90 via standard connectors 36 that are connected to board 90. The height of those connectors may be chosen to provide sufficient clearance between fluid driver 70 and the components on board 90. Rubber spacers may be placed between fluid driver 70 (centered under the hub, for example) and the board in some embodiments to increase impact resistance. The rubber spacers (or spacer) may be glued or otherwise connected to the fluid driver 70 or to board 90.

Figure 10:
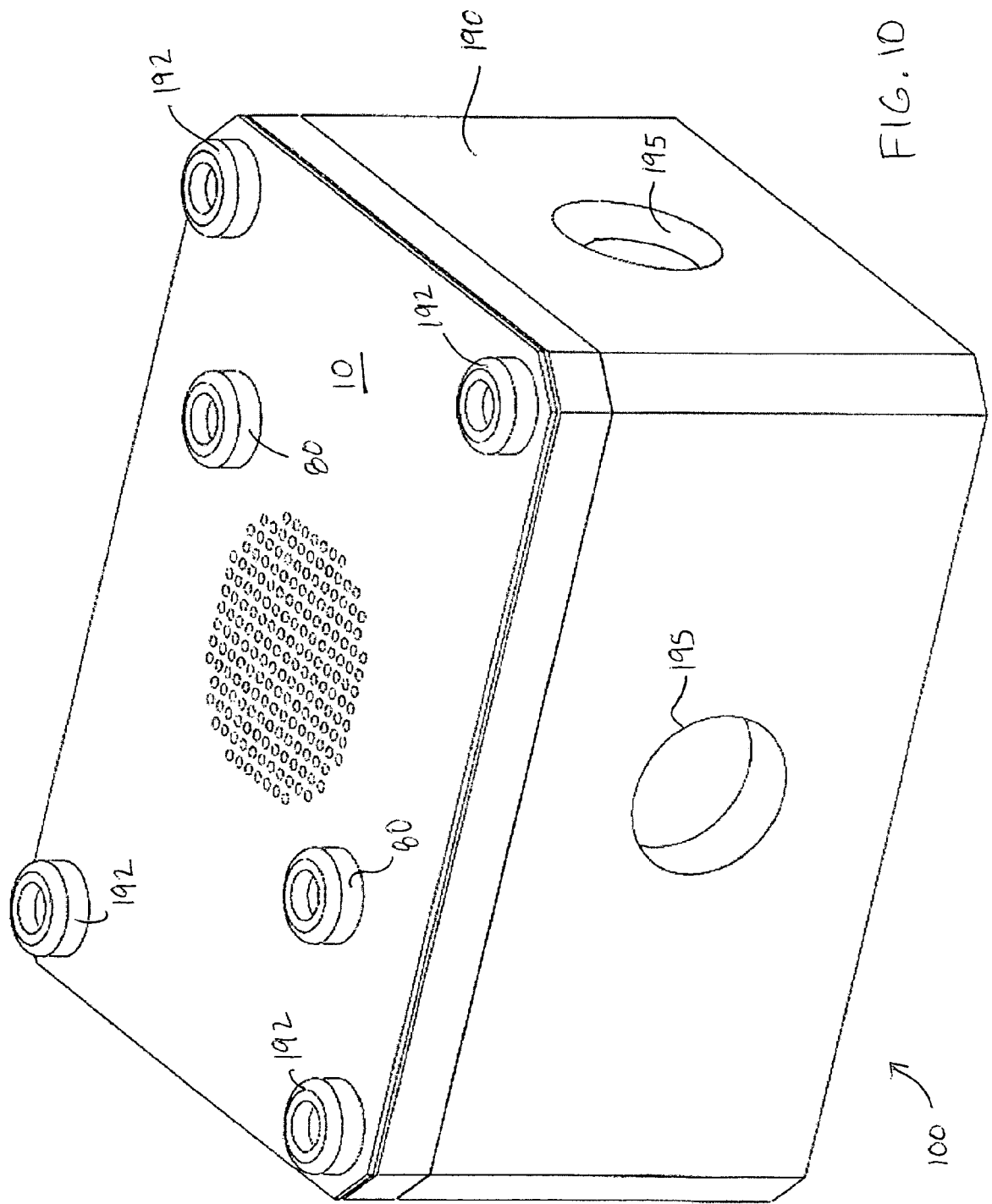
FIG. 10 is a perspective view of one of the present sensors that includes an enclosure.

The present sensors may be substantially enclosed FIG. 10 shows another embodiment of sensor 100 that includes an enclosure 190 that is connected with fasteners 192 (e.g., PLASTITE screws) to flow-guiding structure 25. Enclosure 190 may be a non-metal enclosure made, for example, from unfilled polyamide 612 or 66, and may be useful if additional protection is needed for the SAW devices or other aspects of the sensor. The enclosure need not be heated, and may be characterized as a non-metal unheated enclosure. The enclosure may also have one or more openings 195 in one or more of its sides to help ensure adequate exhaust flow area for the sensor, thus minimizing the pumping requirement of the fluid driver. Although not shown, a filter may be placed over each opening 195. Such a filter may be made from any suitable material, such as a suitable PTFE, one example of which is W. L. Gore & Associates, Inc.'s part number VE41221.

Exemplary circuitry that may be used to drive the SAW devices and detect their outputs is shown and described in U.S. Pat. No. 6,321,588 (the '588 patent) (especially FIG. 1 of the '588 patent), which was incorporated by reference above. Microwave Monolithic Integrated Circuit (MMIC) amplifiers may be used in place of the ASICs 111-116 described in the '588 patent. A selective phase shift network for tuning differences between SAW devices 30 to set the frequency of oscillation of each SAW device may be incorporated anywhere into the '588 patent's closed-loop circuitry. A receiver chip may be used for mixer 120 from the '588 patent to receive and determine the signal strength of each SAW device to determine if the SAW devices 30 are oscillating. The phase shift network may also be incorporated in the oscillator circuit for the reference SAW device to allow the user to tune the reference SAW device frequency and the frequencies of the other (or "sample") SAW devices 30 such that all of the sample SAW device frequencies are either above or below the frequency of the reference SAW device. Using a phase shift network can eliminate the need to use the specific distances recommended by the '588 patent for the length of the conductive paths between the different ASICs and the SAW devices they drive, such that all the oscillator circuits can be tuned to the same desired frequency of oscillation without constraining the actual, physical layout of the circuitry.

The power for the present sensors may come from any suitable source. For example, the SAW driver board 90 may be equipped with a USB port into which a USB cable carrying sufficient power to drive the sensor (including any fluid driver) could be plugged. If the sensor in question is connected to another structure—such as a shaft (e.g., an extendable shaft) or a micro air vehicle—the structure could contain the power source. If the sensor in question is worn on a uniform (e.g., by a soldier), the user could also be wearing a battery pack (see, e.g., FIGS. 12A and 12B) that includes one or more batteries (e.g., lithium ion batteries) that are sized to supply sufficient power to the sensor.

The present sensors may be connected to other structures to form the present devices. For example, FIGS. 11A and 11B illustrate two such devices. Device 300 includes one of the present sensors 100 (having an inlet structure with a different outer configuration than the configuration shown in FIGS. 1 and 2) that has been connected to an unmanned micro air vehicle (MAV) 200 in order to provide a sensor that may be flown into an area to test for the presence of certain chemicals. The inlet structure of the sensor may be positioned flush with the fuselage of MAV 200. In FIG. 11B, device 400 includes one of the present sensors (not visible) connected to MAV 200. However, device 400 differs from device 300 because a scoop 250 has been attached to the fuselage of MAV 200 to further direct fluid to flow into the sensor of device 400. The version of the present sensors that can be used to form device 400 need not include a fluid driver due the use of scoop 250, provided the MAV 200 travels at a rate of 15 miles per hour or more, or the propwash blows air into scoop 250 at an equivalent rate.

One of the present sensors also may be connected to the end of a shaft (e.g., an artificial arm) in such a way that the shaft may be used to extend the effective reach of a human user or fit the sensor into a space too small for a human hand. The shaft may be a telescoping shaft with an effectively variable length. A generic representation of such a device is depicted in FIGS. 12A and 12B, which show device 500 as including a sensor 100 connected to one end of telescoping shaft 550. A user can hold device 500 by handle 575, and either hold processor/power pack 585 in another hand, allow someone else to hold processor/power pack 585, or connect processor/power pack 585 to himself/herself (e.g., attaching it to their clothing or belt). Processor/power pack 585 is connected to sensor 100 via wiring 565.

Figure 13B:
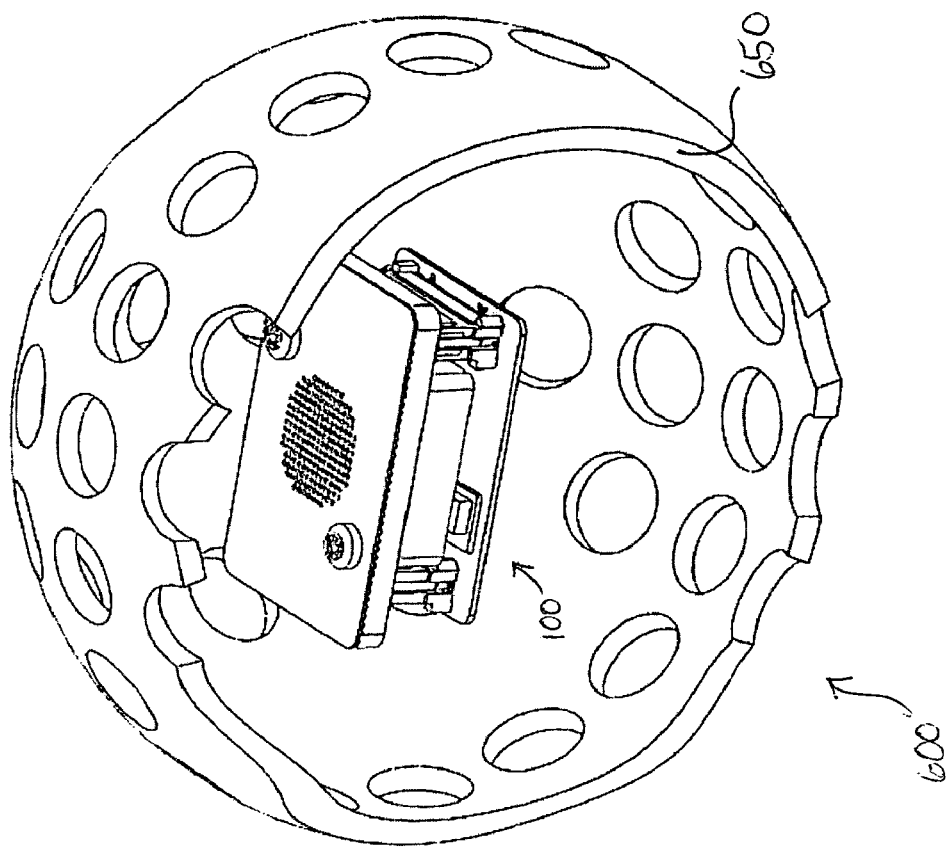
FIGS. 13A and 13B show a perspective view and a partial cut-away view, respectively, of one embodiment of the present devices that includes a sensor connected to a rugged structure.
Figure 13A:
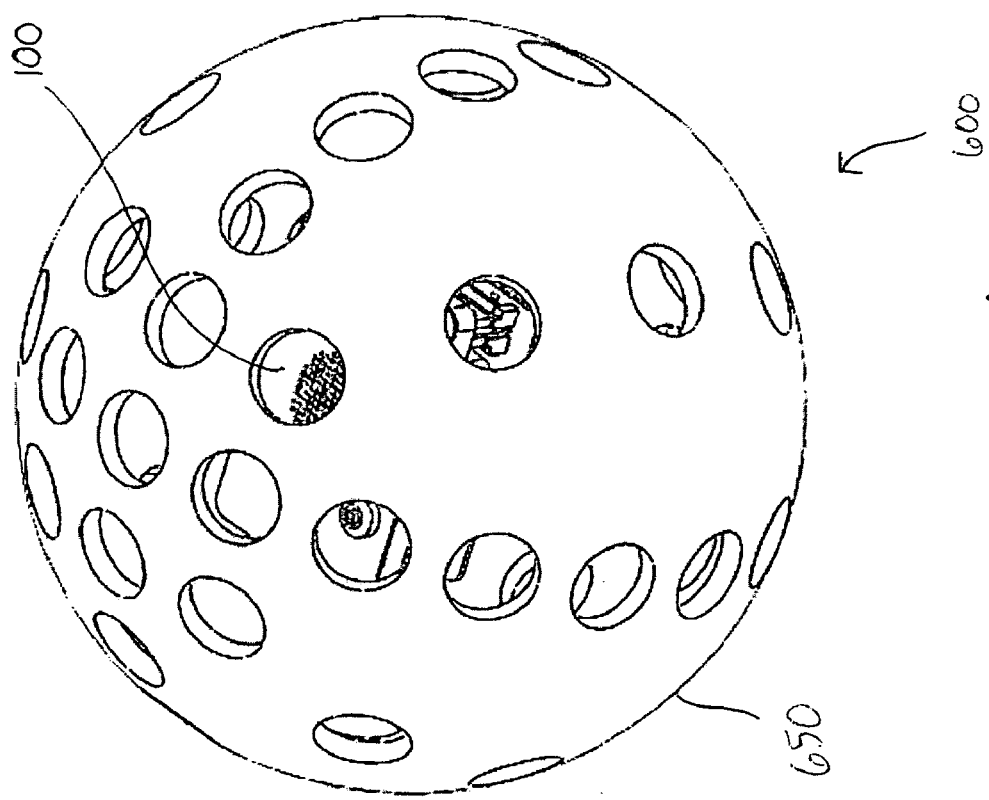

Another device that includes one of the present sensors is a rugged (or ruggedized) structure to which one of the present sensors has been connected. The sensor may be connected such that it is at least partially encased or enclosed (and, in some embodiments, encased or enclosed) in the rugged structure. FIGS. 13A and 13B show device 600, which comprises a rugged structure 650 to which a sensor 100 (represented generically) has been connected (and, in this embodiment, enclosed or encased). More specifically, sensor 100 is enclosed in rugged structure 650. Sensor 100 may be suspended in rugged structure 650 in any suitable way (connection members (such as semi-elastic suspension lines) are not shown) such that fluid can flow into it, and so that the sensor will not be damaged if rugged structure 650 is tossed and hits the ground (e.g., tossed into an open field, into a ravine, down a cliff, into a room, etc.) for the purpose of sensing any chemicals of interest. As shown, rugged structure 650 could be porous, or made to resemble a WHIFFLE ball, such that fluid can easily flow into sensor 100. Device 600 is designed to be a tool that a user (e.g., a soldier) can use as a feasible way of detecting for the presence of a chemical of interest in a location that is not accessible using other devices like device 300, 400 or 500.

Any of the present sensors, including those that form part of any of the present devices, may be equipped with, or coupled to, in any suitable fashion circuitry that is capable of transmitting signals for processing, e.g., such that a determination of whether a target chemical has been sensed can be made, such as through radio frequency (RF) means, hard-wiring, or the like. (Processor/power pack 585 shown generically in FIGS. 12A and 12B could be configured with such processing circuitry.) However, the processing of those signals and the software and/or circuitry required to do the same is not part of the present invention.

The present sensors may be made advantageously small. For example, if manufactured generally to the scale shown in FIG. 2 and as discussed above, a sensor may be less than 2 cubic inches in volume. Furthermore, the present sensors may have a mass of no more than 100 grams in some applications, no more than 75 grams in others, no more than 50 grams in others, and no more than 30 grams in still others (such as a fluid driver-free version of the present sensors that can be used to form device 400).

The smaller the thermal mass (quantified as "heat capacity") of a given embodiment of the present sensors, the smaller its temperature gradient with its surroundings and the quicker it reaches thermal equilibrium with its surroundings. Table 1 below includes exemplary values for the heat capacity of some embodiments of the present sensors. Based on this data, some embodiments of the present sensors have a thermal mass that is no greater than 30 J/K; other embodiments have a thermal mass that is no greater than 20 J/K.

TABLE 1

| Component | Exemplary Material | Exemplary Mass (grams) | Specific Heat Capacity $C_p$ (J/kg-K) | Heat Capacity (J/K) |
|---|---|---|---|---|
| inlet structure 10 | 302SS | 3.75 | 500 | 1.88 |
| flow-guiding structure 25 | Polyamide 612 | 4.25 | 1200 | 5.1 |
| mounting structure 40 | FR4 | 1.5 | 960 | 1.44 |
| SAW driver board 90 | FR4 | 2 | 960 | 1.92 |
| fluid driver 70 | Polybutylene Terephthalate (PBT) | 5.5 | 1200 | 6.6 |
| spacers 60 | polyamide 612 | 0.2 | 1200 | 0.24 |
| orifice plate 50 | 302SS | 0.7 | 500 | 0.35 |
| | | | total | 17.53 |

Embodiments of the present sensors that do not utilize a gas chromatograph may be characterized as sensors that do not include a gas chromatograph. Embodiments of the present sensors that do not utilize a TEC (thermoelectric cooler) to control the base temperature of the SAW devices that are used may be characterized as sensors that do not include a TEC. Embodiments of the present sensors that do not use a heater (e.g., a thin-film heating element) to drive vapors from the SAW devices as part of a SAW-desorbing process may be characterized as sensors that do not include a heater to drive vapors from the SAW devices.

Some prior art sensors, such as the sensors disclosed in the '588 patent, include multiple flow paths that lead to the SAW devices that are used: an ambient flow path and a flow path through which "scrubbed" fluid has flowed. The ambient flow path is designed to carry fluid that may contain a target chemical. The purged flow path is designed to carry "clean" fluid that will help the SAW devices desorb any chemicals that they have absorbed. A scrubber is generally used to purge the air in such sensors, and a valve is generally used to switch between the two flow paths. The scrubbers serve to shorten the time needed by the SAW devices (and, more specifically, the polymers on the SAW devices) to desorb, and thus increase the frequency with which such sensors can be reused. Embodiments of the present sensors that lack a desorbing mechanism (such as a scrubber) may be characterized as sensors that lack a desorbing mechanism, or as sensors that lack a fluid-purging mechanism other than a filter.

The present sensors are modular in nature, and could be positioned side-by-side (in groups of 2, 3, 4 or more) so as to create an array of sensor, each having multiple SAW devices.

It should be understood that the present apparatuses and methods are not intended to be limited to the particular forms disclosed. Rather, they are to cover all modifications, equivalents, and alternatives falling within the scope of the claims. For example, the particular shapes of various features of the present sensors may altered to best suit a given application. In this regard, while the pattern formed by inlet openings 12, filter 15, and flow opening 19 all have circular shapes, other shapes that are better suited to a given application (e.g., rectangular) may be used.

As another example, the flow-guiding structure shown in the figures includes a recessed portion in its top and one in its bottom, thus creating a thinner portion in which flow-guiding openings are positioned. As an alternative, the flow-guiding structure could have the same thickness throughout as the depicted thinner portion, and gaskets having the same depth as the recessed portions shown in the figures could be placed against its top and bottom surfaces to achieve the same configuration shown in the figures (using three structures instead of one structure having two recessed portions).

Furthermore, the outer configuration of, for example, the inlet structure and/or flow-guiding structure of the present sensors can have any suitable shape; the rectangular shape with rounded edges shown in FIGS. 1 and 2 need not be used in every application.

As another example, in an alternative embodiment to what is shown in the figures, orifice plate 50 and spacers 60 could be combined into one molded part made from any suitable material, such as polyamide 612 or 66. Such a combined structure may still be characterized as an orifice plate. Taking this approach could reduce the part count for sensors in which an orifice plate is used, and potentially reduce costs.

As yet another example, instead of utilizing a fluid driver that is substantially parallel with the inlet, flow-guiding and/or mounting structures of the present sensors, some embodiments of the present sensors may utilize an open space positioned downstream of the mounting structure that serves as a plenum, and that is connected to a fluid driver (e.g., a pump) that is remotely positioned. Such embodiments would not include an orifice plate.

The claims are not to be interpreted as including means-plus- or step-plus-function limitations, unless such a limitation is explicitly recited in a given claim using the phrase(s) "means for" or "step for," respectively.

We claim:

1. A sensor comprising:
   an inlet structure;
   a mounting structure that is spaced apart from the inlet structure, the mounting structure having a top surface and an opposing bottom surface; and
   surface acoustic wave (SAW) devices disposed on the top surface of the mounting structure;
   where (a) the mounting structure includes openings that extend from the top surface to the bottom surface through which fluid can flow that has first passed over the SAW devices during operation of the sensor, or (b) the mounting structure and SAW devices together define openings through which fluid can flow that has first passed over the SAW devices during operation of the sensor.

2. The sensor of claim 1 further comprising:
a filter positioned downstream of the inlet structure and upstream of the SAW devices.

3. The sensor of claim 2, where the filter is adhesively secured to the inlet structure.

4. The sensor of claim 2 further comprising:
a flow-guiding structure positioned downstream of the filter and upstream of the SAW devices, the flow-guiding structure including flow-guiding openings, at least one of which is positioned directly over a SAW device.

5. The sensor of claim 4, where the flow-guiding structure includes a flow-guiding structure top surface having a recessed portion from which flow-guiding openings extend and into which fluid flows after first passing through the filter, the recessed portion being defined at least in part by a recessed surface that is below the flow-guiding structure top surface.

6. The sensor of claim 4, where the flow-guiding structure includes at least one flow-guiding opening positioned directly above each SAW device.

7. The sensor of claim 1 further comprising:
a fluid driver positioned downstream of the mounting structure.

8. The sensor of claim 7 further comprising:
an orifice plate positioned downstream of the mounting structure and upstream of the fluid driver, the orifice plate including an opening through which fluid flows after exiting openings in the mounting structure.

9. The sensor of claim 1, where the sensor has a size no greater than 2 cubic inches.

10. The sensor of claim 1, where the sensor has a mass no greater than 100 grams.

11. A sensor comprising:
inlet structure having inlet openings;
a mounting structure that is spaced apart from the inlet structure; and
surface acoustic wave (SAW) devices connected to the mounting structure;
where (a) the mounting structure includes mounting structure openings through which fluid can flow during operation of the sensor, at least one mounting structure opening being positioned adjacent one SAW device, or (b) the mounting structure and SAW devices together define openings through which fluid can flow that has first passed over the SAW devices during operation of the sensor; and
where the mounting structure is oriented such that fluid that flows through the inlet openings and toward the SAW devices will impinge substantially perpendicularly on the SAW devices.

12. The sensor of claim 11 further comprising:
a filter positioned downstream of the inlet structure and upstream of the SAW devices.

13. The sensor of claim 12 further comprising:
a flow-guiding structure positioned downstream of the filter and upstream of the SAW devices, the flow-guiding structure including flow-guiding openings, at least one of which is positioned directly over a SAW device.

14. The sensor of claim 13, where the flow-guiding structure includes at least one flow-guiding opening positioned directly above each SAW device.

15. The sensor of claim 11 further comprising:
a fluid driver positioned downstream of the mounting structure.

16. The sensor of claim 15 further comprising:
an orifice plate positioned downstream of the mounting structure and upstream of the fluid driver, the orifice plate including an opening through which fluid flows after exiting openings in the mounting structure.

17. A sensor comprising:
inlet structure having inlet openings;
a mounting structure that is spaced apart from the inlet structure;
surface acoustic wave (SAW) devices connected to the mounting structure;
a fluid driver positioned downstream of the mounting structure; and
an orifice plate positioned downstream of the mounting structure and upstream of the fluid driver, the orifice plate including an opening through which fluid flows after exiting openings in the mounting structure;
where the mounting structure is oriented such that fluid flowing through the inlet openings and toward the SAW devices will impinge substantially perpendicularly on the SAW devices.

* * * * *